(12) United States Patent
Wang et al.

(10) Patent No.: US 6,358,557 B1
(45) Date of Patent: Mar. 19, 2002

(54) GRAFT POLYMERIZATION OF SUBSTRATE SURFACES

(75) Inventors: Guo-Bin Wang, Rochester; Xianping Zhang, Webster, both of NY (US)

(73) Assignee: STS Biopolymers, Inc., Henrietta, NY (US)

( * ) Notice: Subject to any disclaimer, the term of this patent is extended or adjusted under 35 U.S.C. 154(b) by 0 days.

(21) Appl. No.: 09/394,577

(22) Filed: Sep. 10, 1999

(51) Int. Cl.[7] .................... B05D 3/10; A61L 27/00; A61L 29/00; A61L 31/00
(52) U.S. Cl. .............. 427/2.24; 427/2.25; 427/2.28; 427/2.3; 427/2.31; 427/487; 427/372.2; 427/301; 427/302; 427/303; 427/399; 427/400
(58) Field of Search .............. 427/2.24, 2.25, 427/2.28, 2.3, 2.31, 487, 372.2, 301, 302, 303, 399, 406

(56) References Cited

U.S. PATENT DOCUMENTS

| | | | |
|---|---|---|---|
| 4,331,697 A | | 5/1982 | Kudo et al. |
| 4,377,010 A | * | 3/1983 | Fydelor et al. |
| 4,442,133 A | | 4/1984 | Greco et al. |
| 4,589,964 A | * | 5/1986 | Mayhan et al. ............... 522/85 |
| 4,743,258 A | * | 5/1988 | Ikada et al. |
| 4,978,481 A | * | 12/1990 | Janssen et al. ............... 264/1.4 |
| 5,002,582 A | | 3/1991 | Guire et al. |
| 5,069,899 A | | 12/1991 | Whitbourne et al. |
| 5,211,993 A | | 5/1993 | Kolesinski |
| 5,447,799 A | | 9/1995 | Loh et al. |
| 5,453,467 A | * | 9/1995 | Bamford et al. |
| 5,525,348 A | | 6/1996 | Whitbourne et al. |
| 5,663,237 A | | 9/1997 | Lee et al. |
| 5,741,551 A | * | 4/1998 | Guire et al. ............... 427/407.1 |
| 5,782,908 A | * | 7/1998 | Cahalan et al. |
| 6,013,855 A | | 1/2000 | McPherson et al. |
| 6,096,369 A | * | 8/2000 | Anders et al. |

OTHER PUBLICATIONS

C.–M. Chan et al., "Polymer surface modification by plasmas and photons", *Surface Science Reports*, 24 (1996) 1–54.
R.R. Rye, "Radiation Hardening of Polytetrafluoroethylene Against Chemical Etching", *Journal of Polymer Science: Part B: Polymer Physics*, vol. 26, 2133–2144 (1988).
*Polymer Surfaces from Physics to Technology*, John Wiley & Sons, (1994) pp.223–273.
M.P. Stevens, *Polymer Chemistry an Introduction*, (1975) pp. 196–203.
Shen et al., "A Kinetic Study on MMA Bulk Radical Polymerization", *Polymer International*, 28, (1992) 75–79.

\* cited by examiner

*Primary Examiner*—Shrive P. Beck
*Assistant Examiner*—Jennifer Kolb Michener
(74) *Attorney, Agent, or Firm*—Kenyon & Kenyon

(57) ABSTRACT

The invention includes a method of coating a substrate, comprising exposing a substrate to an initiator capable of initiating a graft polymerization reaction on the substrate, to generate reactive radical sites on the surface of the substrate; contacting the substrate with a composition comprising one or more monomers in a medium which has different hydrophilicity compared to the substrate, and grafting monomer molecules onto the substrate by forming covalent bonds between monomer molecules and the substrate at reactive radical sites on the substrate surface. With the invention, novel coated articles can be obtained which are particularly usefull as medical products such as catheters.

39 Claims, No Drawings

GRAFT POLYMERIZATION OF SUBSTRATE SURFACES

FIELD OF THE INVENTION

The present invention relates to methods for grafting polymers and copolymers onto polymer substrates.

BACKGROUND OF THE INVENTION

It is desirable for substrates such as those used in certain medical devices, including but not limited to catheters and tubes which are inserted into blood vessels, body cavities or tissues, or into the respiratory tract including the trachea, or inserted through other catheters or tubes, to have smoothness to ensure that such devices may be introduced without causing trauma to tissue encountered during their placement. The surfaces may be further enhanced by having lubricity for preventing injury or inflammation of mucous membranes or other surrounding tissues that may be caused when the devices remain in place.

In some instances, it is advantageous for medical device surfaces to have the capability to serve as a depot for various physiologically or pharmacologically active agents. Anti-thrombogenic materials, such as complexes of heparin with quaternary ammonium compounds, have been used on medical device surfaces to prevent thrombus formation on the surface of a medical device, as described in U.S. Pat. No. 5,069,899. In order to control nosocomial infections, anti-microbial agents including penicillins, cephalosporins, fluoroquinolones, aminoglycosides, silver compounds, phenols, biguanides, and others, have been proposed for use in surface coatings on the surfaces of implanted prostheses, as described in U.S. Pat. Nos. 5,069,899 and 4,442,133.

Many of the plastic materials of which such devices are ordinarily constructed are not easily treated with conventional surface enhancing methods. Materials used to make catheters are mostly hydrophobic and resist to one degree or another treatments designed to make them more biocompatible. Polymers such as silicones, latex rubbers, polyolefins, and many polyesters and polyamides have very low surface energies, often less than 40 dynes/cm$^2$. Furthermore, these surfaces are often very resistant to dissolution in or swelling by solvents that ordinarily are used in the coating industry. Also, these surfaces often lack functional groups susceptible to interactions such as hydrogen bonding or Van der Waals forces, which are commonly utilized to promote improved adhesion of surface layers. Technologies that have been proposed to overcome these shortcomings fail to address a number of the difficulties associated with the surface treatment of such medical devices.

Flame treatments are widely applied in surface modification to introduce oxygen-containing functions at polyolefin surfaces, mainly to improve printability or paintability. (F. Garbassi, M. Morra, E. Occhiello, *Polymer Surfaces, From Physics to Technology*, John Wiley & Sons, Chichester, (1994)). Active species formed by the high temperatures include radicals, ions, and molecules in excited states. Such treatments have not been used widely in the medical device industry. The harsh conditions of flame treatments generally could be harmful to the relatively fragile devices, and they have not been useful in treating device lumens.

Corona treatments exploit the corona affect, i.e. the formation of high energy electromagnetic fields close to thin wires or points, with consequent ionization in their proximity, even at atmospheric pressure and relatively low temperatures. Excited species (ions, radicals, electrons, molecules in excited states, etc.) are present in the ionized region, and are active in surface modification, typically the introduction of oxygen-containing functions. (F. Garbassi, M. Morra, E. Occhiello, *Polymer Surfaces, From Physics to Technology*, John Wiley & Sons, Chichester, (1994)). Although this process may be suitable for treating film webs, it is not suitable for treating device lumens and has not found wide application in the medical device industry.

"Cold Plasma" treatments require low pressure to be sustained at low temperatures. An ionized region is formed, including high energy photons, electron, ions, radicals, and excited species, with its composition depending on a gas feed. Low pressure plasmas can be employed for surface activation by the introduction of oxygen-containing functional groups, etching by formation of gaseous species (e.g., carbon oxides or fluorides in $CF_3/O_2$ plasmas), or coating deposition by plasma polymerization (e.g., of fluorine or silicon-containing monomers). (F. Garbassi, M. Morra, E. Occhiello, *Polymer Surfaces, From Physics to Technology*, John Wiley & Sons, Chichester, (1994)). Cold plasma treatments have been used in the medical device industry but generally have not been effective at treating device lumens that are long or of small diameter.

"Hot Plasma" treatments are performed at atmospheric pressure at very high temperatures (5,000 to 10,000° K.). While these treatments have gained widespread use in the metallurgy industry, they generally are not useful with polymeric medical devices because of the extremely high temperatures that are required.

Ultraviolet (UV) treatments employ photons, usually having low wavelength and high energy, which are used to activate a variety of chemical reactions. A typical example of UV action on polymer surfaces is surface degradation by sun exposure. UV lamps have been used for the treatment of polymer surfaces, with the apparatus involving a lamp and sample illumination devices. A review of literature on UV-cured coatings can be found in C.-M. Chan, T.-M. Ko, and H. Hiraoka, *Surf. Sci. Rep.*, 24,1 (1996), and R. R. Rye, *J. Polym. Sci. Phys.* Ed. 26, 2133 (1988). UV-induced graft polymerization is used to treat and modify medical devices. However such treatment has limited application. Many medical devices are deliberately treated to make them opaque to such radiation, and it is difficult to treat device lumens, especially smaller, longer lumens, unless the device is transparent to the UV radiation.

Free radical graft copolymerization has been used to modify material surfaces. Highly reactive free radical transferring creates reactive radical sites on the substrate surface, which are able to initiate copolymerization with available monomers, or reactive oligomers, thereby generating a graft polymer layer. Two major difficulties with such an approach are the ability to create a substantial number of substrate radicals, and to significantly reduce the amount of homopolymerization initiated by initiator radicals along with the graft copolymerization. (M. P. Stevens, Polymer chemistry: an introduction, Addison-Wesley, London(1975)).

Graft polymerization of medical catheters and other medical devices has been utilized to provide surfaces having different properties from the bulk polymers forming the body of the device. Such treatments typically use plasma or UV as a source of energy to promote the graft polymer formation and attendant covalent bonding to the surface.

In U.S. Pat. No. 5,447,799, Loh, et al. describe a process for depositing polymeric materials on surfaces, first by providing a layer of polymeric material on the surface by glow discharge polymerization of a mixture of silane and a vaporizable hydrocarbon monomer or a vaporizable organosilane monomer, and then providing a second layer of another polymeric material, on the first polymeric material, by vapor deposition polymerization of aromatic hydrocarbons or unsaturated hydrocarbons.

Kolesinski et al. U.S. Pat. No. 5,211,993 describes a method of preparing chromatographically active support material by coating surfaces of a comminuted inorganic substrate material with a monomer which, when polymerized, has chromatographic properties. Such monomers are said to include vinyl stearate, polyethylene glycol 1000 monomethacrylate, and stearyl methacrylate. Such treatments have the shortcoming of requiring expensive plasma generating apparatus to modify the device surface.

U.S. Pat. No. 5,741,551 describes methods for providing a polymer coating on a solid substrate by applying a coating of reactive chemicals having photo-activatable ketones covalently bonded to them, and irradiating with UV light to induce covalent bonding of the reactive chemicals to the substrate, followed by reacting a layer of monomer, oligomer, or polymer with the covalently bound reactive chemicals to produce a polymeric layer which is covalently bound to the substrate. U.S. Pat. No. 5,002,582 describes a method of applying a polymer coating onto a substrate that involves coating a surface with a mixture of polymer and polymer having covalently bound photo-activatable groups, and irradiating the material with UV light to induce covalent bonding of the coating to the substrate. These methods require radiation sources and are not suitable for the effective application of lumen coatings.

Lee, et al. U.S. Pat. No. 5,663,237 describes that graft polymer layers can be created on plastic surfaces by heating a mixture of monomer(s), polymerization initiator, and a supercritical solvent which is capable of at least superficial penetration into the device plastic surface in a pressure reactor. Disadvantages of the method include the need for high pressure and temperature, the presence of harmful reactive polymerization initiator in the graft polymer layer, the need for "supercritical" solvents to penetrate the device surface, and the inability to use the technique on surfaces for which supercritical solvents are unavailable.

A need exists for a means of providing polymer coatings on surfaces, particularly on surfaces such as polyolefins (such as polyethylene), silicones, polyamides, latex rubber, etc., onto which it is difficult for conventionally applied coatings to adhere. There is a particular need for providing polymer coatings in a convenient, inexpensive manner, and to apply coatings to the exterior and interior surfaces of devices.

SUMMARY OF THE INVENTION

The present invention relates to polymeric substrates and treatments which form polymers and modify the surface properties of the substrate. The invention includes a method of coating a substrate, comprising exposing a substrate with an initiator capable of initiating a graft polymerization reaction on the substrate; generating reactive radical sites on the surface of the substrate; contacting the substrate with a composition comprising a monomer in a medium which optionally has reversed phase properties compared to the substrate, in terms of hydrophilicity; and grafting the monomers onto the substrate by forming covalent bonding at reactive radical sites on the substrate surface, and accomplishing graft polymerization.

Preferably, the invention employs a salting out effect to favor graft polymerization instead of homopolymerization of the monomers. The invention permits graft polymerization of substrates at relatively low operating and capital costs, can accommodate polymerization of substrates of varied shapes, and can be utilized in relatively large batch operations. The invention is particularly useful in coating the lumen of polymeric substrates of varying dimensions, which are useful as medical devices.

The invention comprises a method of providing a solid surface with desired characteristics comprising contacting a substrate with an initiator of similar hydrophilicity as the substrate, and contacting the substrate with a medium having a surface tension that differs from the surface energy of the substrate, and in which the initiator is poorly soluble. Optionally the medium has reversed phase properties in terms of hydrophilicity, compared to the substrate. The medium preferably contains monomers having desired surface characteristics for the polymer substrate. The medium preferably is subject to mixing during contact with the substrate, to promote uniform dispersion of the monomer. The reaction preferably is performed at temperatures from about 20° C. to about 100° C. and at pressures from about 0.5 atmosphere to about 50 atmospheres. Optionally, the medium can contain salts or other materials having a relatively high solubility in the medium.

Suitable media include, but are not limited to, organic solvents and aqueous solutions, optionally containing dissolved ions or other substances which are very soluble in the medium and which will encourage graft polymerization. Suitable initiators include but are not limited to peroxide initiators, azo initiators, redox initiators, and photo-initiators/photosensitizers/thermal initiators. Hydrophilic or hydrophobic monomers can be used. Optionally, one or more cross-linking agents can be employed, such as cross-linking agents containing di- or multi-unsaturated functional groups. One embodiment of the present invention comprises a method of coating a lumen of a device by a reverse phase graft polymerization method described herein.

The present invention is applicable to a variety of substrates, including medical devices comprising silicone, polyethylene, polyamide and latex. With the invention, such devices can undergo surface modification by reversed phase graft polymerization, providing the device with altered surface characteristics, such as improved lubriciousness, and/or the ability to serve as a drug reservoir.

Thus, according to the invention, polymers and copolymers can be grafted onto polymer substrates to provide a surface with various finctions, including but not limited to hydrophilicity, lubricity, ability to serve as a primer or tie coat, and ability to serve as a reservoir for physiologically or pharmacologically active agents. The reversed-phase graft polymerization of the instant invention permits hydrophilic polymer coatings on difficult-to-adhere-to surfaces, is capable of being applied to both interior an exterior surfaces of devices, and is relatively convenient and inexpensive.

DETAILED DESCRIPTION OF THE PREFERRED EMBODIMENTS

The invention provides methods for graft polymerization, preferably reversed-phase graft polymerization, enabling the grafting of polymers and copolymers onto polymer substrates in order to serve a variety of functions. Examples include, but are not limited to, the use of a graft polymer capable of absorbing large quantities of water in order to provide moisture absorption or lubricity; the use of the graft polymer as a tie coat in order to allow succeeding layers to adhere; the use of the graft polymer to provide functional groups to attach physiologically or pharmacologically active agents; and the use of the graft polymer as a drug depot permnitting the delivery of various drugs from the graft polymer. Optionally drugs can be mixed in with the polymer or bound to the finctional groups with ionic forces.

Devices that could be provided with different surface characteristics by this method include but are not limited to medical devices, including but not limited to catheters, guide wires and medical instruments. Examples include, but are not limited to, PTCA catheters, cardiology catheters, central venous catheters, urinary catheters, drain catheters, and dialysis catheters.

Properties which can be provided to devices of the invention include, but are not limited to, hydrophobic coatings on hydrophilic substrates, hydrophilic coatings on hydrophobic substrates, non-conductive coatings on conductive surfaces, conductive coatings on non-conductive surfaces, acidic or basic coatings on pH-neutral substrates, non-thrombogenic coatings on thrombogenic substrates, thrombogenic coatings on non-thrombogenic substrates, and coatings with radio-isotopic magnetic, antibiotic and anti-cancer properties.

According to the invention, a graft polymerization is performed by selecting an appropriate initiator and a polymerization medium, based on the nature of the substrate and the required surface properties. Appropriate initiators preferably will orient free radicals to attack the substrate surface and create the reactive radical sites on the substrate necessary to initiate graft polymerization. The graft polymerization generates a surface polymer layer as a surface coating which adheres well to various substrates, including polymer substrate surfaces which are difficult to adhere to.

Many inert surface materials have low surface energy. In the present invention, media with surface tensions of a magnitude differing from the surface energy of the substrate are selected in order to perform the process of modifying this group of materials. Optionally, for hydrophobic substrates, hydrophobic initiators and hydrophilic media are selected. Most preferably, the medium, on the one hand, and the substrate and the initiator, on the other hand, have a sufficiently different hydrophilicity so that the reaction will favor graft polymerization on the substrate instead of homopolymerization in the medium. The properties of the modified surface reflect the properties of the graft copolymer which in turn depend on the monomers chosen. The monomers preferably are sufficiently dissolved in the medium to permit the graft polymerization reaction to occur. Alternatively, monomers can be dispersed in the medium by suspension. Preferably, if the substrate is hydrophilic, hydrophilic initiators are used, if hydrophobic, preferably hydrophobic initiators are used.

The substrate can be of any suitable formn or shape, including but not limited to tubing, sheets, fibers, strips, films, plates, filaments, pellet resins, powders, and extruded, molded or cast articles. Optionally, the substrate can comprise a medical device, including but not limited to catheters and drains. The substrate can be hydrophobic or hydrophilic.

The method of the present invention preferably comprises dissolving or dispersing one or more monomers in a medium containing an appropriate solvent or solvent mixture. The substrate or substrates are coated or otherwise contacted with the initiator, such as a solution containing the initiator, and optionally then dried. Optionally, the solution containing the initiator can contain a small amount of polymer which is soluble in the medium to adhere the initiator on the substrate temporarily. Preferably, the initiator is coated or otherwise placed onto the substrate surface prior to contacting the substrate with the medium. However, the initiator optionally can be placed in the medium, either alone or in conjunction with coating or otherwise placing it on the substrate.

The monomer solution comprises suitable concentrations of appropriate monomers, preferably at a concentration from about 2 to about 6 w/w %, in a medium selected based on the properties of the substrate and monomer. Preferably, an initiator-coated substrate is placed in a reaction vessel which contains the monomer solution. Optionally, the substrate, uncoated with initiator, can be paced into a reaction vessel which contains the initiator in the medium. Preferred reaction vessels include those having glass or stainless steel surfaces.

Preferably, the system is degassed by vacuum to prevent air bubbles forming between the reversed-phase substrate-solution interface, and then the graft polymerization reaction is allowed to proceed. However, degassing is not required. The presence of oxygen is not believed to significantly affect the graft polymerization reaction. Preferably, the reaction is conducted under an ambient atmospheric gas mixture. However, the reaction can be conducted under any suitable gas mixture, including nitrogen, argon, helium and neon.

The graft polymerization reaction pressure preferably is less than about 50 atmospheres, preferably from about 0.5 to about 50 atmospheres, more preferably from about 0.5 to about 10 atmospheres, and even more preferably from about 0.75 to about 3 atmospheres. A reaction pressure of about 1 atmosphere is most preferred.

The graft polymerization reaction preferably is conducted at a temperature in the range from about from about 10° C. to about the boiling point of the medium solvent at the employed pressure. At atmospheric pressure, using an aqueous solvent, the reaction temperature preferably is less than about 100° C. More preferably, the reaction temperature is from about 40° C. to about 90° C., and most preferably from about 80° C. to about 90° C., at atmospheric pressure. At pressures higher than atmospheric, the reaction can take place at higher temperatures. Suitable reaction times can range from about ten minutes up to several hours, or longer. Monomer reactivity and initiator decomposition are related to temperature. Generally, the reaction rate is increased with increased temperature, allowing a shorter reaction time. The upper limit of the reaction temperature is governed by the boiling point of the medium, and the thermal tolerance of the substrate, at the reaction pressure.

The process can be accelerated by removing any inhibitor which was included with the monomer source to prolong monomer shelf life, especially when high levels of inhibitors or low reactivity monomers are used. However, generally it is unnecessary to remove the inhibitor contained in the monomer.

Preferably, the medium is stirred during the time it is in contact with the substrate to promote graft polymerization. If the substrate is in the form of a hollow tube, or contains a lumen, preferably the medium is pumped through the lumen in order to promote graft polymerization of the interior surface or lumen of the substrate. The reaction system often contains solid substrate and liquid medium and in that sense is heterogeneous. Also, differences in hydrophilicity between the medium and the substrate can cause the heterogeneous nature of the system. Promoting homogeneity of the medium and availability of monomers in the region surrounding the substrate, e.g., by maintaining a relatively uniform temperature, can contribute to the uniformity of the graft coating. Therefore, moderate, continued stirring of the medium preferably is maintained during the reaction. However, overly vigorous stirring can slow graft polymerization, and is disfavored.

After the reaction has been completed to a sufficient degree, the substrate can be removed from reaction with the medium, either by removing the substrate from the vessel, or by removing the medium from the vessel. Any undesired monomers or polymers remaining in the graft layer may be removed by washing. Although initiators tend to remain attached to the substrate surface, they can decompose at elevated temperatures and become smaller fragments which can be removed easily. Any residual monomer, homopolymer, initiator, and decomposed fragments of initiator which are present on the substrate can be removed by washing in appropriate solvents at elevated temperature, and discarded. Suitable washing solvents include those which can dissolve monomers, homopolymers, initiator or initiator fragments but do not deform the substrate.

Hydrophobic substrates useful in this invention include but are not limited to solid synthetic or natural polymer materials. The substrate preferably is a solid, but the invention can include other suitable substrates, for example, cross-linked hydrogels. The preferred solid substrate materials include, but are not limited to: polyolefins, including but not limited to polyolefins such as polyethylene and polypropylene, polyisobutylene and ethylene-alphaolefin copolymers; silicone polymers; acrylic polymers and copolymers, including but not limited to polyacrylonitrile, polymethylmethacrylate, polyethylmethacrylate, polyethylacrylate, and other polyesteracrylates and polyestermethacrylates; fluoropolymers, including but not limited to polytetrafluoroethylene, chlorotrifluoroethylene, fluorinated ethylene-propylene, and polyvinyl fluoride; vinyl polymers, including but not limited to polyvinyl chloride, polyvinyl methyl ether, polystyrene, polyvinyl acetate, and polyvinyl ketones; vinyl monomer-containing copolymers, including but not limited to ABS; natural and synthetic rubbers, including but not limited to latex rubber, butadiene-styrene copolymer, polyisoprene, polybutadiene, butadiene-acrylonitrile copolymers, polychloroprene polymers, polyisobutylene rubber, ethylene-propylenediene copolymers, and polyisobutylene-isoprene; polyurethanes, including but not limited to polyetherurethanes, polyesterurethanes, polycarbonateurethanes and polysiloxaneurethanes; and polyamides, including but not limited to Nylon 6, Nylon 66, Nylon 10, and Nylon 11; polyesters; epoxy polymers; wool; cotton; silk; rayon; cellulose; and modified celluloses.

Hydrophilic substrates preferably are solids and include, but are not limited to: hydrophilic acrylic polymers, including but not limited to polyacrylamide, poly-2-hydroxyetbylacrylate, poly-N,N'-dimethylacrylamide, polyacrylic acid, and polymethacrylic acid; vinyl polymers, including but not limited to poly-N-vinylpyrrolidone, and polyvinylpyridine; polymaleic acid; poly-2-hydroxyethyl fumarate; maleic anhydride; starch and polyvinyl alcohol.

The medium is selected according to the nature of the substrate and the particular substrate surface modification desired. The medium preferably does not appreciably dissolve the substrate, and most preferably does not result in any dissolution or swelling of the substrate. It is particularly preferred that the medium and substrate have significant differences in their relative hydrophilicity. For example, if a hydrophilic substrate is used, a hydrophobic medium preferably is chosen and if a hydrophobic substrate is used, a hydrophilic medium preferably is chosen. One benefit of employing substrate and medium materials with different relative hydrophilicity, such as materials with reversed phase properties in terms of hydrophilicity, is that this can increase the efficiency of generating substrate radicals. Also, homopolymerization of the monomer can be limited by the lack of the radicals in the medium. Although not wishing to be bound by theory, it is believed that, as a result of differences in hydrophilicity in the system, initiator radicals or organic propagating radicals are directed to and attack the substrate, rather than the monomers in the medium.

In a preferred embodiment, the invention includes a salting out effect to favor graft polymerization. To employ a salting out effect, materials, such as salts, that are characterized by relatively high solubility in the medium are included in, or added to, the medium to force the monomer (s) toward the substrate phase. Preferred salting agents include, but are not limited to, sodium, ammonium, and potassium salts.

In processes for modification of the surface of a hydrophobic substrate, a hydrophilic media preferably is employed. Aqueous solutions preferably are used as the media, more preferably containing ion strength reinforcing agents. Preferably, ions or buffers, including sodium, ammonium, potassium, chloride, phosphate, and acetate are used. In processes for modifying hydrophilic substrates, a hydrophobic medium preferably is used. In such processes, the preferred media is an organic solvent, preferably containing one or more of toluene, hexane, cyclohexane, benzene, xylene, tetrahydroftiran, and aliphatic alcohols. Although preferred, it is not necessary that the solvent be non-toxic.

Preferred media include from about 3% w/w to about 6% w/w acrylamide derivatives, from about 0.1% w/w to about 0.4% w/w diacrylate crosslinker, from about 10% w/w to about 20% w/w sodium chloride and from about 0.01% w/w to about 0.03% w/w polyvinylpyrrolidone; or from about 1.0% w/w to about 3.0% w/w acrylamide derivatives, from about 3.0% w/w to about 5% w/w polyethylene glycol acrylate, from about 10% w/w to about 20% w/w sodium chloride and from about 1.0% w/w to about 3.0% w/w polyvinylpyrrolidone.

The initiator should have an affinity for, and preferably similar hydrophilicity to, the selected substrate, and should be relatively insoluble or poorly soluble in the medium in order to reduce homopolymerization in the medium. The initiator should be capable of generating at least one, and preferably two or more, free-radicals with an affinity for the substrate, permitting the free radicals to attack the substrate surface to create functional groups capable of reacting with the monomer.

If highly hydrophobic organic initiators with symmetrical structures can generate two hydrophobic initiator free-radicals, this class of initiators can have a higher efficiency of initiator free-radical transference to the hydrophobic substrate than initiators that generate only one hydrophobic initiator radical. The insolubility or poor solubility of the initiator in the medium can limit initiator free-radical diffusion into the medium, and thereby inhibit initiation of homopolymerization of the monomers in the medium. Initiators that can be used in the practice of the present invention include, but are not limited to peroxides, azo initiators, redox initiators, photo initiators and photosensitizers which can be thermally initiated. Particularly preferred initiators include organic peroxides.

Optionally, thermal initiators (including but not limited to peroxide and azo initiators), and redox initiators can be used to perform graft polymerization on inner surfaces of the substrate, including but not limited to lumen surfaces if the devices comprising the substrate are hollow. Under appropriate initiation conditions, these initiators permit both the free radicals and monomers in the liquid medium to access the lumen and to perform graft polymerization. Thermal initiators can give relatively constant initiation rates during the process, while the initiation rate for redox initiators can decline quickly because of the rapid consumption of initiator components. Initiation by radiation, with and without proteolytic initiators, also can be useful in the invention, although such initiators can be somewhat limited in usefulness in lumens, since the penetration of the radiation through the wall of the lumen reduces the intensity of the radiation.

Preferred peroxide initiators include, but are not limited to, peroxyesters, including but not limited to 1,1-dimethyl-3-hydroxybutyl peroxyneodecanoate, α-cumyl peroxyneodecanoate, α-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di(2-ethylhexanoylperoxy)hexane, t-butylperoxy-2 ethylhexanoate, t-butylperoxyacetate, t-amylperoxyacetate, t-butylperbenzoate, t-amylperbenzoate, and t-butyl-1-(2-ethylhexyl)monoperoxycarbonate; peroxyketals, including but not limited to, 1,1-di(t-butylperoxy)-3,3,5-trimethylcyclohexane, 1,1-di(t-butylperoxy)-cyclohexane, 1,1-di(t-amylperoxy)-cyclohexane, ethyl-3 ,3-di(t-butylperoxy)-butyrate, and ethyl-3 ,3-di(t-amylperoxy)-butylperoxy)-butylrate; peroxydicarbonates, including but not limited to di(n-propyl)peroxydicarbonates, di(sec-butyl) peroxydicarbonates, and di(2-ethylhexyl) peroxydicarbonates; ketone peroxides, including but not limited to 2,4-pentanedione peroxide; hydroperoxides, including but not limited to cumene hydroperoxide, butyl hydroperoxide, and amyl hydroperoxide; dialkyl peroxides, including but not limited to dicumyl peroxide, dibutylperoxide, and diamylperoxide; diacyl peroxide, including but not limited to decanoyl peroxide, lauroyl peroxide, and benzoyl peroxide; and inorganic peroxides, including but not limited to hydrogen peroxide and potassium persulfate, and mixtures of the above.

Preferred azo initiators include but are not limited to azobisisobutyronitrile, azobiscumene, azo-bisiso-1,1,1-tricyclopropylmethane, 4-nitrophenyl-azo-triphenylmethane, and phenyl-azo-triphenylmethane. Preferred redox initiators include, but are not limited to, peroxide-amine systems, peroxide-metal ion systems, and boronalkyl-oxygen systems, such as are described in Hans-Georg Elias, *Macromolecules,* Plenum Press (New York, 1984). Photo initiators/photosensitizers which can be thermally initiated, include, but are not limited to, organic peroxide and azo initiators, benzophenone, benzophenone derivatives, and catnphorquinone-N,N dimethyl-aminoethyl-methacrylate.

The monomers in the present invention preferably should be selected so as to accomplish the desired graft polymerization reaction, and to provide compatibility with the substrate, and to impart the desired properties to the substrate. The term monomer is used to refer to both monomeric and oligomeric forms of molecules. Free radical polymerizable monomers or oligomers can be used in the invention. Preferably, vinyl monomers, and more preferably acrylic monomers, are used in the invention. To perform the graft coating if the monomers used are relatively, or even completely, insoluble in the medium, monomer suspensions could be made using dispersing agents, including but not limited to polyvinyl alcohol, and barium sulfate. Optionally, the addition of alcohol could increase the solubility of the monomers, to achieve the desired concentration in the medium.

Suitable hydrophilic monomers include, but are not limited to, hydroxyl substituted ester acrylate and ester methacrylate, including but not limited to 2-hydroxyethylacrylate, 2- and 3-hydroxypropylacrylate, 2,3-dihydroxypropylacrylate, polyethoxyethyl-, and polyethoxypropylacrylates; acrylamide, methacrylamide and its derivatives, including but not limited to N-methylacrylamide, N,N-dimethylacrylamide, N,N-dimethylmethacrylamide, N,N-dimethyl-aminoethyl, N,N-diethyl-aminoethyl, 2-acrylamido-2-methyl-1-propanesulfonic acid, N-[3-dimethylamino)propyl] acrylamide, and 2-(N,N-diethylamino)ethyl methacrylamide; polyethylene glycol acrylates, polyethylene glycol methacrylates, polyethylene glycol diacrylates, polyethylene glycol dimethacrylates; polypropylene glycol acrylates, polypropylene glycol methacrylates, polypropylene glycol diacrylates, polypropylene glycol dimethacrylates; acrylic acid; methacrylic acid; 2- and 4-vinylpyridine; 4- and 2-methyl-5-vinylpyridine; N-methyl-4-vinylpiperidine; 2-methyl-1-vinylimidazole; dimethylaminoethyl vinyl ether; N-vinylpyrrolidone; itaconic, crotonic, fumaric and maleic acids, and mixtures thereof.

Hydrophobic monomers include, but are not limited to, ester acrylates and ester methacrylates including but not limited to methyl, ethyl, propyl, butyl, phenyl, benzyl, cyclohexyl, ethoxyethyl, methoxyethyl, ethoxypropyl, hexafluoroisopropyl and n-octyl-acrylates and -methacrylates; acrylamides and methacrylamides; dimethyl fumarate, dimethyl maleate, diethyl fumarate, methyl vinyl ether, ethoxyethyl vinyl ether, vinyl acetate, vinyl propionate, vinyl benzoate, acrylonitrile, styrene, alpha-methylstyrene, 1-hexene, vinyl chloride, vinyl methyl ketone, vinyl stearate, 2-hexene and 2-ethylhexyl methacrylate, and mixtures thereof.

Optionally, cross-linking agents can be used to provide a cross-linked polymer structure. Suitable agents include, but are not limited to, monomers having di- or multi-unsaturated functional groups, including but not limited to diacrylates and dimethylacrylates of -polyethylene glycol and -polypropylene glycol, trimethylolpropane triacrylate and trimethacrylate, di-trimethylolpropane, tetraacrylate, pentaerythritol tetraacrylate, and tetramethacrylate, divinylbenzene, divinyl sulfone silicone-containing diacrylates and dimethacrylates.

Many polymeric polymer devices are made of polymers, such as silicone rubber, polyethylene, and polypropylene, which have a hydrophobic surface. In many applications for these devices, it is desirable that the device have a hydrophilic, lubricious surface. For example, catheters used in angioplasty and angiographic procedures preferably are lubricious and hydrophilic, to promote ease of transport from the point of insertion to the desired position for imaging or treatment, such as a cardiac ventricle. With the invention, hydrophilic monomers, such as N-vinylpyrrolidone, acrylamide and derivatives, can form wet lubricious polymer coatings on the surface of a hydrophobic medical device, by reversed phase graft polymerization. Since the present invention allows the monomer solution to contact the inner lumen of hollow devices, lumen surface modification is readily performed.

With the invention, monomers substituted containing functional groups can be used, to provide functional groups on the polymer surface. Two significant applications for providing such functional groups on the polymer surface are to attach physiologically or pharmacologically active agents to the polymer and to employ the graft polymer as a tie coat for other coatings which otherwise might not adhere to the substrate. With the present invention, graft polymers can be created which contain functional groups to which biological agents such as penicillins, cephalosporins, fluoroquinolones, aminoglycosides, silver compounds, phenols, and biguanides can be attached. Monomers having functional groups including, but not limited to, carboxylic acid, amine, hydroxyl, and polyethylene glycol could be used in order to provide these functional groups on the surface after graft coating.

With the invention, monomers may also be used that may or may not contain functional groups and which can serve to provide the surface with properties such as wet lubricity, hardness, softness, or other physical properties. Such graft layers may also be used as a reservoir so that materials, such as drugs, can be entrapped in the graft layer and can be leached out when placed in moist environments, such as inside human patients. This can provide targeted drug delivery to various sites within the body. Typical drugs which can be entrapped within the graft layers include, but are not limited to, anti-infective agents, such as antibiotics (including aminoglycosides such as gentimicin and amikacin), antimicrobial agents, such as benzalkonium chloride, 2-bromo-2-nitropropane-1,3-diol (Cosmosil), and polyhexanide (Bronopol); antithrombogenic compounds, such as benzalkoniumheparinate, and trididecylmethylammonium heparinate; anticancer agents, such as paclitaxel, merbarone, and methotraxate; anti-inflammatories, such as dexamethasone; and other agents as may be desired. In this way, the agents may be entrapped with or without covalent interactions with functional groups that may or may not exist on the graft polymer(s), and one or both mechanisms (entrapment and covalent bonding) could be operating within a layer simultaneously. Also, the graft polymers can act as tie coats to other layers which can serve as drug reservoirs.

Since the coating is covalently bonded to the substrate, the surface coating in the present invention has strong adhesion to the substrate. The yield of graft polymer can be controlled, by changing the surface area and factors such as initiation rate, temperature, and monomer concentration, which influence molecular weight in traditional free radical polymerization. Accordingly, the amount and size of side chains can be controlled with the invention.

A preferred embodiment of the present invention comprises treating a silicone substrate by dip-coating the substrate with an initiator comprising an organic peroxide solution, preferably a 1 to 10% solution, in tetrahydrofuran (THF). Thereafter, the substrate is air-dried and placed in a medium comprising about 3.9 w/w % N,N-dimethylacrylamide and about 0.19 w/w % acrylamide, about 0.25 w/w % diacrylate crosslinker, about 15% w/w sodium chloride and about 0.02 w/w % polyvinylpyrrolidone. The system is optionally degassed and the reaction is performed at a temperature from about 20° C. to about 100° C., more preferably from about 80° C. to about 90° C., most preferably from about 85° C. to about 89° C., and at a pressure from about 0.5 atmospheres to about 50 atmospheres, more preferably from about 0.5 atmospheres to about 3 atmospheres. The reaction preferably is permitted to proceed for up to about 3 hours while there is gentle mixing of the medium by a magnetic stirrer. This system provides graft layers of reasonable smoothness on the substrate surface; a longer reaction could produce thicker, rougher coats.

Another preferred embodiment of the present invention comprises coating a silicone substrate with an initiator comprising organic peroxide solution, at a concentration of about 1 to 10 w/w %, preferably about 6 w/w %, in tetrahydrofiran (THF). The substrate can be air dried and then placed into a medium comprising 1.9 w/w % acrylamide, 4.3 w/w % polyethylene glycol acrylate, 14.5 w/w % sodium chloride, and 2.0 w/w % polyvinylpyrrolidone. The reaction is performed at a temperature from about 20° C. to about 100° C., more preferably from about 80° C. to about 90° C., most preferably from about 85° C. to about 89° C., and at a pressure from about 0.5 atmospheres to about 50 atmospheres, more preferably from about 0.5 atmospheres to about 3 atmospheres. At a temperature of about 85° C. to about 89° C., and a pressure of about 1 atmosphere, the reaction is permitted to proceed for up to about 50 minutes while there is gentle mixing of the medium.

In another preferred embodiment, reverse phase graft polymerization is used to produce a surface coating on a substrate for use as a primer, or tie coat. A preferred method includes coating a substrate, such as a silicone substrate with an initiator comprising organic peroxide solution, about 1 to 10 w/w %, preferably about 6 w/w %, in tetrahydrofuran (THF), followed by dip-coating in a solution comprising 1 w/w % polyurethane, 12% acrylic polymer, 1.2% epoxy polymer, 64.1% THF, 10.2% methyl ethyl ketone, 10% ethylene glycol monobutyl ether and 1.5% polyethylene glycol, and then drying, preferably at about 85° C. for up to about 4 hours.

In another preferred embodiment, non-reverse phase graft coating is used to produce a surface coating on a difficult to adhere to substrate for use as a primer, or tie coat. A preferred method could include coating a substrate, such as a silicone substrate with an initiator comprising organic peroxide such as benzoyl peroxide, 1 to 10 w/w % in tetrahydrofuran, allowing to air dry. The treated substrate could then be dipped in a solution comprising 10 to 15 w/w % acrylic monomer(s) in 64.1% THF, 10.2% methylethylketone, 1.5% polyethylene glycol, 5% hydroxyethylmethacrylate, and the balance ethylene glycol monobutyl ether at 60° C., for a period of four hours in a reflux condenser. This would produce a graft polymer layer on the silicone surface to which various polymer coatings would adhere well. Such polymer layers would include but not be limited to polyurethanes, acrylics, polyamides, cellulosics and others.

The following Examples are illustrative of the invention, and are not intended to limit the scope of the invention.

EXAMPLE 1

Medical-grade colorless silicone tubing (Helix Medical, 3.18 mm outer diameter×1.58 mm internal diameter×20 cm length), was first treated by standard dip-coating in an 8 w/w % benzoyl peroxide solution in tetrahydrofuran (THF) for 30 seconds. The tubing was air dried and then placed in a 6 cm×40 cm glass cylinder, open at one end, containing 800 gm of an aqueous monomer solution composed of 3.9 w/w % N,N-dimethylacrylamide and 0.19 w/w % acrylamide, 0.25 w/w % diacrylate crosslinker, 15 w/w % sodium chloride and 0.02 w/w % polyvinylpyrrolidone. The system was degassed at 1.0 mm Hg for 10 minutes. The reactor was placed in a water bath at 87° C. for 3 hours, and the reaction system was stirred gently on a magnetic stirrer. After 3 hours, the tubing was removed from the reactor and washed with water.

The treated tubing was tested for lubricity. This coating was strongly adherent to the substrate and decreased the coefficient of friction to 6.8% of the original coefficient, from 183 g for the uncoated substrate to 12.5 g after coating, when the samples were pulled with 70.8 g weight against polyvinyl chloride under deionized water.

TABLE 1

Contact angles (θ) of graft coated silicone rubber and silicone rubber control

| Samples | Control | | Graft Coating | |
|---|---|---|---|---|
| Measurement | Advancing θ | Receding θ | Advancing θ | Receding θ |
| Run 1 | 108.36 | 78.08 | 103.9 | 26.68 |
| Run 2 | 109.22 | 81.63 | 101.26 | 28.33 |
| Run 3 | 107.99 | 78.02 | 106.66 | 37.74 |

A sample of the graft-coated tubing also was dipped in 2.0 w/w % of solution of gentian violet in water and alcohol, then taken out immediately and rinsed under a running tap of deionized water for 5 minutes. Following the rinse, the coating had a blue staining indicating a hydrophilic surface.

EXAMPLE 2

Medical-grade colorless silicone tubing (Helix Medical, 3.18 mm outer diameter×1.58 mm internal diameter×20 cm length), was treated by standard dip-coating in 8 w/w % benzoyl peroxide in tetrahydrofuran (THF) for 30 seconds. The tubing was air dried and then placed in a 6 cm×40 cm glass cylinder, open at one end containing 800 gm of an aqueous monomer solution composed of 1.9 w/w % acrylamide, 4.3 w/w % polyethylene glycol acrylate, 14.5 w/w % sodium chloride and 2.0 w/w % polyvinylpyrrolidone. The system was degassed at 1.0 mm Hg for 10 minutes. The reactor was placed in a water bath at 87° C. for 50 minutes and the reaction system was stirred gently on a magnetic stirrer. After 50 minutes the tubing was removed from the reactor and washed with water.

A sample of the tubing was stained using the method described in Example 1, and showed a blue staining which indicated the presence of a hydrophilic surface on the substrate. After drying, the sample then was elongated up to 350%. After elongation, the sample returned to its original configuration with no evidence of cracking, crumbling, or delamination, and the visual appearance of the sample remained the same as prior to elongation.

The graft coated and stretched sample of the tubing was tested for graft adhesion. A strip of adhesive tape (Scotch tape (3M)) was pressed firmly over the sample and removed quickly. No blue coating spots adhered to the tape.

Unstretched coated samples were soaked for 5 minutes in aqueous solutions containing antimicrobial agents with w/w concentrations as shown in Table 2, and then rinsed with deionized water. They were air dried and then incubated for 24 hours at 37° C. on standard method agar against *S. aureus,* and evaluated by zone of inhibition. The inhibition zone diameter of the treated samples against *S. aureus* is given in Table 2.

TABLE 2

Inhibition zone diameter (four runs) against *S. aureus*

| | Zone size (mm) | |
|---|---|---|
| Antimicrobial | Uncoated silicone tubing (control) | Graft coated silicone tubing |
| 4.8% rifamycin | 17, 19, 20, 26 | 32, 33, 33, 35 |
| 1.9% gentamicin lauryl sulfate | Not tested | 12, 12, 12, 13 |
| 2% vantocil | 0, 0, 0, small | 9, 9, 10, 10 |
| 4.8% benzalkonium chloride | 0, 0, small, small | 16, 16, 16, 16 |
| 2% 2-bromo-2-nitropropane-1,3-diol | Not tested | 38, 38, 38, 38 |
| 2% silver nitrate | Not tested | 11, 12, 12, 12 |
| 2% Germall plus | Not tested | 8, 8, 8, 8 |
| 1% methotraxate | Not tested | 10, 11, 11, 11 |
| 1% paclitaxel | Not tested | 6, 6, 6, 7 |

EXAMPLE 3

Interior coated samples made according to Example 1 were placed in a monomer solution made according to Example 2, composed of 1.9 w/w % acrylamide, 4.3 w/w % polyethylene glycol acrylate, 14.5 w/w % sodium chloride, and 2.0 w/w % polyvinylpyrrolidone. A graft polymerization reaction was performed using the procedure set forth in Example 1, except that instead of stirring, the reaction solution was circulated vertically upwardly through the tubing by a roller pump. After 50 minutes the tubing was removed from the reactor, and washed with water.

A sample of the tubing was stained using the method described in Example 1, and a blue color on the interior surface of the tubing indicated the presence of the coating on the inner surface of the tubing.

EXAMPLE 4

Initiator-coated samples made according to Example 1 and silicone tubing samples without initiator coating were placed in a monomer solution made according to Example 2. Graft polymerization was performed according to the procedure used in Example 1. After graft polymerization, the samples that were not coated with initiator were rinsed and stained using the method of Example 1. The blue dyed surface indicated the presence of the graft coating on these samples. This demonstrates that initiator can diffuse through the medium and cause graft polymerization without inducing significant homopolymerization

EXAMPLE 5

Samples cut from a latex rubber glove (VWR Scientific Products, Inc.) were dip-coated with an initiator solution, in the same method set forth in Example 1. Then, graft polymerization was performed using an aqueous monomer solution composed of 1.9 w/w % acrylamide , 4.3 w/w % of polyethylene glycol acrylate, 14.5 w/w % sodium chloride, and 2.0 w/w % polyvinylpyrrolidone, using the procedures set forth in Example 1. After polymerization, the samples were stained as described in Example 1. The blue stain demonstrated that a graft coating was obtained.

EXAMPLE 6

Pieces of polyurethane tubing (Thermedics Inc.) were graft coated using the method described in Example 5. The coated samples were stained according to the method of Example 1. The significant blue staining demonstrated that graft coating on the surface.

EXAMPLE 7

Pieces of polyethylene tubing were dip-coated with an initiator solution comprising 8 w/w % benzoyl peroxide in tetrahydrofuran (THF) for 30 seconds. The tubing was air dried and then placed in a long reactor containing an aqueous medium comprising 30.0 w/w % acrylamide, 2.0 w/w % polyvinylpyrrolidone, 15.0 w/w % sodium chloride. The system was degassed at 1.0 mm Hg for 10 minutes. The reactor was placed in a water bath at 85° C. for 40 minutes and the reaction system was stirred gently on a magnetic stirrer. After 40 minutes the tubing was removed from the reactor and washed with water. The sample was stained according to the method described in Example 1, which indicated a hydrophilic coating on the surface.

EXAMPLE 8

Samples of medical-grade colorless silicone tubing (Helix Medical, 3.18 mm outer diameter×1.58 mm internal diameter×20 cm length) were treated according to the method described in Example 2. The dry tubing samples were dip-coated in a solution comprising 1 w/w % polyurethane, 12% acrylic polymer, 1.2% epoxy polymer, 64. 1% THF, 10.2% methyl ethyl ketone, 10% ethylene glycol monobutyl ether and 1.5% polyethylene glycol, and then dried at 85° C. for 4 hours. An adhesion test was conducted according to the method of Example 1, and the samples passed the test.

EXAMPLE 9

A piece of medical grade Tygon tubing lionyvinylchloride) was graft-coated according to Example 1. The sample was then stain tested according to Example 1, and the staining demonstrated the presence of a hydrophilic grafi-coating of the sample surface.

What is claimed is:

1. A method of coating a substrate, comprising:
   exposing a substrate to an initiator in solution capable of initiating a graft polymerization reaction on the substrate, to generate reactive radical sites on the surface of the substrate;
   contacting the exposed substrate having reactive radical sites with a composition comprising one or more monomers in a medium which has reversed phase properties compared to the substrate, in terms of hydrophilicity and further comprising a solute in an amount sufficient to induce a salting-out effect; and
   graft polymerizing onto the substrate by forming covalent bonds between monomer molecules and the substrate at reactive radical sites on the substrate surface.

2. The method of claim 1, further comprising mixing the composition so that a plurality of said molecules remain in proximity to said reactive radical site.

3. The method of claim 1, wherein the monomers are grafted onto the substrate at a pressure less than about 50 atmospheres.

4. The method of claim 1, wherein the monomers are grafted onto the substrate at a temperature from about 10° C. to about 100° C.

5. The method of claim 1, wherein the substrate is selected from the group consisting of solid synthetic polymers and solid natural polymers.

6. The method of claim 5, wherein the substrate is selected from the group consisting of polyolefin, silicone polymer, acrylic polymer, acrylic copolymer, polyesteracrylate, polyestermethacrylate, fluoropolymer, vinyl polymer, vinyl monomer-containing copolymer, natural rubber, synthetic rubber, polyurethane, polyamide, polyester, epoxy polymer, wool, cotton, silk, rayon, and cellulose.

7. The method of claim 6, wherein the substrate is selected from the group consisting of polyethylene, polypropylene, polyisobutylene, ethylene-alphaolefin copolymer, polyacrylonitrile, poly(methyl methacrylate), poly(ethyl methacrylate), poly(ethyl acrylate), poly (tetrafluoroethylene), poly(chlorotrifluoroethylene), fluorinated ethylene-propylene, poly(vinyl fluoride), poly(vinyl chloride), poly(vinyl methyl ether), polystyrene, poly(vinyl acetate), poly(vinyl ketone), ABS rubber, latex rubber, butadiene-styrene copolymer, polyisoprene, polybutadiene, butadiene-acrylonitrile copolymer, polychloroprene polymer, polyisobutylene rubber, ethylene-propylenediene copolymer, poly(isobutylene/isoprene), polyetherurethane, polyesterurethane, polycarbonateurethane and polysiloxaneurethane, Nylon 6, Nylon 66, Nylon 10, Nylon 11, modified cellulose, polyacrylamide, poly(2-hydroxyethylacrylate), poly(N,N'-dimethylacrylamide), poly(acrylic acid), polymethacrylic acid, poly(N-vinylpyrrolidone), polyvinylpyridine, polymaleic acid, poly (2-hydroxyethyl fumarate), maleic anhydride, starch, and poly(vinyl alcohol).

8. The method of claim 1, wherein the medium is a hydrophilic aqueous solution.

9. The method of claim 8, wherein the solute is selected from the group consisting of water soluble chloride salt, water soluble phosphate salt, or water soluble acetate salt.

10. The method of claim 8, wherein the solute is selected from the group consisting of water soluble sodium salt, water soluble potassium salt, and water soluble ammonium salt.

11. The method of claim 8, wherein the solute is selected from the group consisting of sodium chloride, potassium chloride, ammonium chloride.

12. The method of claim 8, wherein the solute is present in a concentration greater than about 0.5 moles per liter.

13. The method of claim 12, wherein the solute is present in a concentration greater than about 2 moles per liter.

14. The method of claim 1, wherein the medium is hydrophobic, and comprises an organic solvent.

15. The method of claim 1, wherein the solution comprises a water soluble polymer.

16. The method of claim 15, wherein the solute is a non-ionic species with high solubility in the medium.

17. The method of claim 16, wherein the non-ionic species is and poly(vinylpyrrolidone).

18. The method of claim 14, wherein the medium comprises a solvent selected from the group consisting of toluene, hexane, cyclohexane, and mixtures thereof.

19. The method of claim 1, wherein the initiator is selected from the group consisting of peroxide initiators, azo initiators, redox initiators, and photoinitiators/photosensitizers which can be thermally initiated.

20. The method of claim 19, wherein the initiator is a peroxide initiator selected from the group consisting of peroxyester, peroxyketal, peroxydicarbonate, ketone peroxide, dialkyl peroxide, diacyl peroxide, an inorganic peroxide, and mixtures thereof.

21. The method of claim 19, wherein the initiator is selected from the group consisting of 1,1-dimethyl-3-hydroxybutyl peroxyneodecanoate, α-cumyl peroxyneodecanoate, α-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di (2-ethylhexanoylperoxy)hexane, t-butylperoxy-2-ethylhexanoate, t-butylperoxyacetate, t-amylperoxyacetate, t-butylperbenzoate, t-amylperbenzoate, t-butyl-1-(2-ethylhexyl)monoperoxycarbonate, 1,1-di(t-butylperoxy)-3,3,5-trimethyl-cyclohexane, 1,1-di(t-butylperoxy)-cyclohexane, 1,1-di(t-amylperoxy)-cyclohexane, ethyl-3,3-di(t-butylperoxy)-butyrate, ethyl-3,3-di(t-amylperoxy)-butylperoxy)-butylrate, di(n-propyl)peroxydicarbonate, di(sec-butyl)perosydicarbonate, di(2-ethylhexyl) peroxydicarbonate, 2,4-pentanedione peroxide, cumene hydroperoxide, butyl hydroperoxide, amyl hydroperoxide, dicumyl peroxide, dibutylperoxide, diamylperoxide, decanoyl peroxide, lauroyl peroxide, benzoyl peroxide, hydrogen peroxide, potassium persulfate, and mixtures thereof.

22. The method of claim 19, wherein the initiator is an azo initiator selected from the group consisting of azobisisobutyronitrile, azobiscumene, azo-bisiso-1,1,1-tricyclopropylmethane, 4-nitrophenyl-azo-triphenylmethane phenyl-azo-triphenylmethane, and mixtures thereof.

23. The method of claim 19, wherein the initiator is a redox initiator selected from the group consisting of peroxide-amine systems, peroxide-metal ion systems, and boronalkyl-oxygen systems.

24. The method of claim 1, wherein the monomer is selected from the group consisting of hydrophilic monomers and hydrophobic monomers.

25. The method of claim 24, wherein the monomer comprises a hydrophilic monomer selected from the group consisting of hydroxyl substituted ester acrylate, ester methacrylate, 2-hydroxyethylacrylate, 2-hydroxypropylacrylate, 3-hydroxypropylacrylate, 2,3-dihydroxypropylacrylate, polyethoxyethylacrylate, polyethoxypropylacrylate, acrylamide, methacrylamide, N-methylacrylamide, N,N-dimethylacrylamide, N,N-dimethylmethacrylamide, N,N-dimethyl-aminoethyl, 2-acrylamido-2-methyl-1-propanesulfonic acid, N,N-diethyl-aminoethyl, 2-acrylamido-2-methyl-1-propanesulfonic acid, N-[3-dimethylamino)propyl] acrylamide, 2-(N,N-diethylamino)ethyl methacrylate, polyethylene glycol acrylate, polyethylene glycol methacrylate, polyethylene glycol diacrylate, polyethylene glycol dimethacrylate; polypropylene glycol acrylate, polypropylene glycol methacrylate, polypropylene glycol diacrylate, polypropylene glycol dimethacrylate; acrylic acid, methacrylic acid, 2- and 4-vinylpyridine; 4- and 2-methyl-5-vinylpyridine, N-methyl-4-vinylpiperidine, 2-methyl-1-vinylimidazole, dimethylaminoethyl vinyl ether, N-vinylpyrrolidone, itaconic acid, crotonic acid, flumaric acid, maleic acid, and mixtures thereof.

26. The method of claim 24, wherein the monomer comprises a hydrophobic monomer selected from the group consisting of ester acrylates selected from the group consisting of methyl, ethyl, propyl, butyl, phenyl, benzyl, cyclohexyl, ethoxyethyl, methoxyethyl, ethoxypropyl, hexafluoroisopropyl and n-octyl-acrylates; ester methacrylates selected from the group consisting of methyl, ethyl, propyl, butyl, phenyl, benzyl, cyclohexyl, ethoxyethyl, methoxyethyl, ethoxypropyl, hexafluoroisopropyl and n-octyl-methacrylates; acrylamides; methacrylamides; dimethyl fumarate; dimethyl maleate; diethyl fumarate; methyl vinyl ether; ethoxyethyl vinyl ether; vinyl acetate; vinyl propionate; vinyl benzoate; acrylonitrile; styrene; alpha-methylstyrene; 1-hexene; vinyl chloride; vinyl methyl ketone; vinyl stearate; 2-hexene; 2-ethylhexyl methacrylate, and mixtures thereof.

27. A method of coating a substrate, comprising:

exposing a substrate to an initiator in solution capable of initiating a graft polymerization reaction on the substrate, to generate reactive radical sites on the surface of the substrate;

contacting the substrate with a composition comprising one or more monomers in a medium which has reversed phase properties compared to the substrate, in terms of hydrophilicity and a concentration of a solute sufficient to induce a salting-out effect, while mixing the composition;

graft polymerizing onto the substrate by forming covalent bonds between monomer molecules and the substrate at reactive radical sites on the substrate surface; and contacting the substrate with a cross-linking agent.

28. The method of claim 27, wherein the cross-linking agent is selected from the group consisting monomers having di- or multi-unsaturated functional groups.

29. The method of claim 28, wherein the cross-linking agent is selected from the group consisting of diacrylates of poly(ethylene glycol), diacrylates of poly(propylene glycol), dimethylacrylates of poly(ethylene glycol), dimethylacrylates of poly(propylene glycol), trimethylolpropane triacrylate, trimethylolpropane trimethacrylate, di-trimethylolpropane, tetraacrylate, pentaerythritol tetraacrylate, tetramethacrylate, divinylbenzene, divinyl sulfone, silicone-containing diacrylates and dimethacrylates, and mixtures thereof.

30. The method of claim 1, wherein the composition further comprises a water soluble polymer.

31. The method of claim 30, wherein the water soluble polymer is poly(vinylpyrollidone).

32. The method of claim 31, wherein the poly (vinylpyrollidone) is present in a concentration from about 0.01 weight percent to about 3.0 weight percent.

33. The method of claim 30, wherein the substrate is silicone;

the initiator is an organic peroxide solution in tetrahydrofuran (THF);

the medium comprises from about 3% w/w to about 6% w/w acrylamide derivatives, from about 0.1% w/w to about 0.4% w/w diacrylate crosslinker, from about 10% w/w to about 20% w/w sodium chloride and from about 0.01% w/w to about 0.03% w/w poly (vinylpyrrolidone); and, the reaction is allowed to proceed at a temperature from about 80° C. to about 95° C. at atmospheric pressure.

34. The method of claim 30, wherein the substrate is silicone;

the initiator is an organic peroxide solution in tetrahydrofuran (THF);

the medium comprises from about 1.0% w/w to about 3.0% w/w acrylamide derivatives, from about 3.0% w/w to about 5% w/w polyethylene glycol acrylate, from about 10% w/w to about 20% w/w sodium chloride and from about 1.0% w/w to about 3.0% w/w poly(vinylpyrrolidone); and the reaction is allowed to proceed at a temperature from about 80° C. to about 95° C. at atmospheric pressure.

35. The method of claim 30, wherein the substrate is polyethylene;

the medium comprises from about 20% w/w to about 40% w/w acrylamide, from about 1% w/w to about 3% w/w polyvinylpyrrolidone, and from about 10% w/w to about 20% w/w sodium chloride; and the reaction is allowed to proceed at a temperature from about 80° C. to about 95° C. at atmospheric pressure.

36. The method of claim 1, wherein the substrate is selected from the group consisting of silicone, polyethylene, polyamide and latex, and wherein the grafting coats the substrate surface with a coating having characteristics selected from the group consisting of lubricious, hydrophilic and elastic properties.

37. The method of claim 1, further comprising attaching to the coated substrate a biological agent selected from the group consisting of penicillins, cephalosporins, fluoroquinolones, aminoglycosides, silver compounds, phenols, and biguanides.

38. A method of coating a substrate, comprising:

exposing a substrate to an initiator in solution capable of initiating a graft polymerization reaction on the substrate, to generate reactive radical sites on the surface of the substrate;

contacting the substrate with a composition comprising one or more monomers in a medium and a concentration of a solute sufficient to induce a salting-out effect; and graft polymerizing onto the substrate at a pressure less than about 50 atmospheres by forming covalent bonds between monomer molecules and the substrate at reactive radical sites on the substrate surface.

39. The method of claim 38, wherein said graft polymerization is accomplished at a pressure less than about 10 atmospheres.

* * * * *

UNITED STATES PATENT AND TRADEMARK OFFICE
CERTIFICATE OF CORRECTION

PATENT NO.    : 6,358,557 B1
DATED         : March 19, 2002
INVENTOR(S)   : Wang, Zhang et al.

It is certified that error appears in the above-identified patent and that said Letters Patent is hereby corrected as shown below:

<u>Title page,</u>
Item [57], ABSTRACT,
Line 12, change "usefull" to -- useful --

<u>Column 4,</u>
Line 47, change "finctions" to -- functions --

<u>Column 5,</u>
Line 4, change "finctional" to -- functional --
Line 52, change "formn" to -- form --

<u>Column 7,</u>
Line 51, change "hydroxyetbylacrylate" to -- hydroxyethylacrylate --

<u>Column 8,</u>
Line 28, change "tetrahydroftiran" to -- tetrahydrofuran --

<u>Column 9,</u>
Line 50, change "catnphorquinone" to -- camphorquinone --

<u>Column 12,</u>
Line 2, change "tetrahydrofiran" to -- tetrahydrofuran --

<u>Column 15,</u>
Line 35, change "lionyvinylchloride" to -- polyvinylchloride --
Line 38, change "grafi-coating" to -- graft-coating --

UNITED STATES PATENT AND TRADEMARK OFFICE
CERTIFICATE OF CORRECTION

PATENT NO. : 6,358,557 B1
DATED : March 19, 2002
INVENTOR(S) : Wang, Zhang et al.

It is certified that error appears in the above-identified patent and that said Letters Patent is hereby corrected as shown below:

<u>Column 16,</u>
Line 50, delete "and"

Signed and Sealed this

First Day of October, 2002

*Attest:*

*Attesting Officer*

JAMES E. ROGAN
*Director of the United States Patent and Trademark Office*